United States Patent
Fontana et al.

(10) Patent No.: US 7,468,438 B2
(45) Date of Patent: Dec. 23, 2008

(54) PROCESS FOR THE SEMISYNTHESIS OF DESERPIDINE

(75) Inventors: Gabriele Fontana, Milan (IT); Ezio Bombardelli, Groppello Cairoli (IT); Cristian Samori, Forli' (IT); Eleonora Baldelli, Bologna (IT); Andrea Guerrini, Bologna (IT); Arturo Battaglia, Bologna (IT); Bruno Danieli, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/593,651

(22) PCT Filed: Mar. 2, 2005

(86) PCT No.: PCT/EP2005/002190

§ 371 (c)(1), (2), (4) Date: Jun. 18, 2008

(87) PCT Pub. No.: WO2005/095394

PCT Pub. Date: Oct. 13, 2005

(65) Prior Publication Data

US 2008/0242864 A1  Oct. 2, 2008

(30) Foreign Application Priority Data

Mar. 25, 2004  (IT) .......................... MI2004A0582

(51) Int. Cl.
*C07D 459/00* (2006.01)
*C07D 491/22* (2006.01)

(52) U.S. Cl. .......................................... 546/55; 546/40

(58) Field of Classification Search .................. 546/55, 546/40
See application file for complete search history.

(56) References Cited

FOREIGN PATENT DOCUMENTS

GB  809913  3/1959
GB  868478  5/1961

OTHER PUBLICATIONS

Sakai et al., "The Chemical Transformation to Deserpidine", Heterocycles, vol. 10, 1978, pp. 67-71.
Tamiz et al., "Structure-Activity Relationship for a Series of 2-Substituted 1,2,3,4-Tetrahydro-9H-Pyrido[3,4-b]Indoles: Potent Subtype-Selective Inhibitors of N-Methyl-D-Aspartate (NMDA) Receptors", Bioorganic & Medicinal Chemistry Letters, vol. 9, 1999, pp. 1619-1624.

*Primary Examiner*—Charanjit S Aulakh
(74) *Attorney, Agent, or Firm*—Mathews, Shepherd, McKay & Bruneau, P.A.

(57) ABSTRACT

The present invention relates to an efficient procedure for the synthesis of deserpidine (Ia), starting from reserpic acid lactone (II) via the intermediate 11-O-demethyl reserpic acid lactone (III).

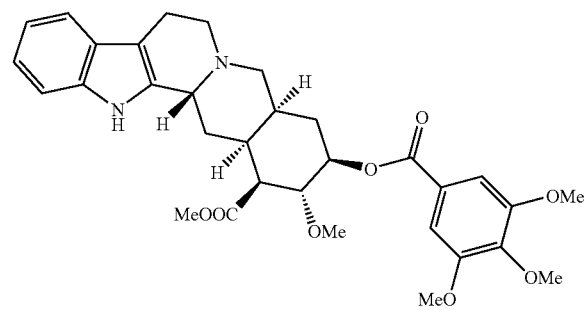

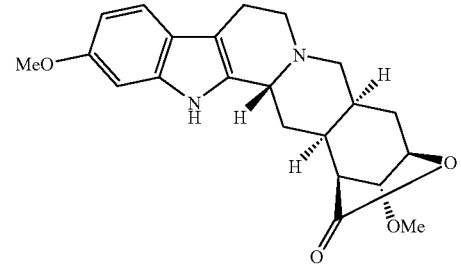

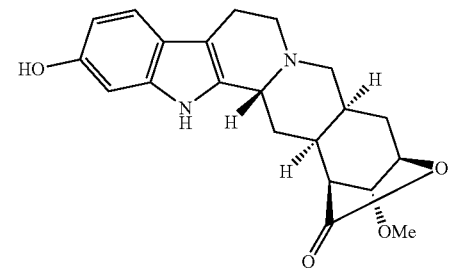

9 Claims, No Drawings

PROCESS FOR THE SEMISYNTHESIS OF DESERPIDINE

FIELD OF THE INVENTION

The present invention relates to indole alkaloids, in particular to a process for the synthesis of deserpidine.

BACKGROUND OF THE INVENTION

Reserpine (Ib) was isolated for the first time in 1952 from *Rauwolfia serpentina* extracts by Schlitter (Muller et al, Experientia 1952, 8, 338) and identified as the main responsible for the ipotensive activity of *Rauwolfia* spp extracts.

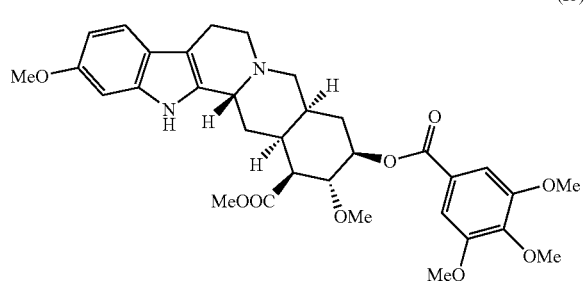

Deserpidine (Ia) was isolated for the first time in 1955 from *Rauwolfia canescens* roots by Hofmann (Stoll and Hofmann, *J. Am. Chem. Soc.* 1955, 77, 820).

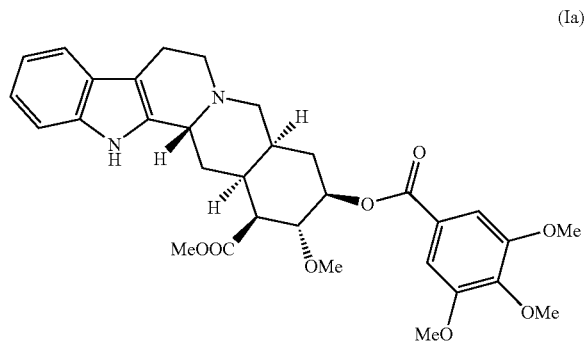

Over the years reserpine and related indole alkaloids, such as deserpidine, have played an important role in the treatment of hypertensive, nervous and mental disorders. Even if deserpidine has an interesting pharmacological profile, its use has always been limited compared with reserpine due to its poor availability in nature. In fact, deserpidine titre in the cortical part of the roots is of about 0.003-0.005%, whilst reserpine titre is of about 0.1-0.2%.

Deserpidine is structurally related to reserpine (Ib) and rescinainmine (Ic).

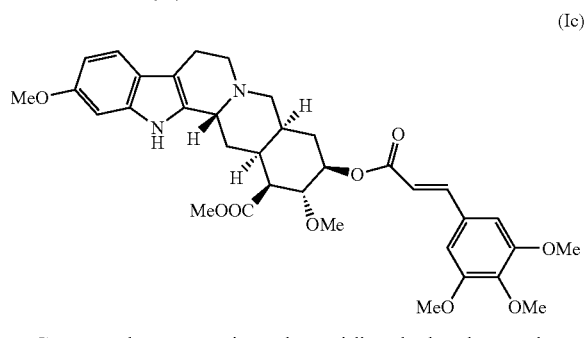

Compared to reserpine, deserpidine lacks the methoxy group at the 11-position. Compared to rescinnamine, deserpidine lacks the methoxy group at the 11-position and is esterified at the 18-position with a 3,4,5-trimethoxybenzoic residue instead of a 3,4,5-trimethoxycinnamic residue.

Theoretically, the conversion of reserpine to deserpidine could be carried out through demethoxylation of the 11-position. According to known organic chemistry methods, the easiest way could be either the direct demethoxylation of reserpine or the conversion of the 11-methoxy group to hydroxy group, followed by reduction of the phenol ring to benzene ring.

It is known to those skilled in the art that the polyfunctionalization of reserpine, rescinnamine and methyl reserpate (Id)

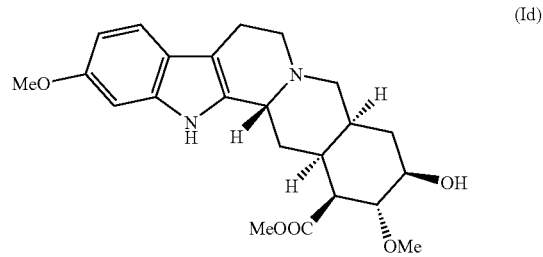

does not allow selective O-demethylation of the hydroxy group at the 11-position. The known methods for direct 11-demethoxyation or 11-O-demethylation lack regioselectivity and/or chemoselectivity.

It has now been found that these problems can be overcome using reserpic acid lactone as the precursor.

DETAILED DESCRIPTION OF THE INVENTION

The present invention relates to a process for the synthesis of deserpidine which comprises demethylation of reserpic acid lactone, conversion of the phenol ring to benzene ring and re-esterification of the 18-hydroxy group.

In more detail, the process comprises the following steps:

a) demethylation of reserpic acid lactone (II)

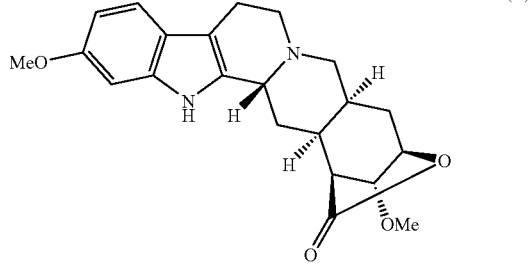

to give 11-O-demethyl reserpic acid lactone (III)

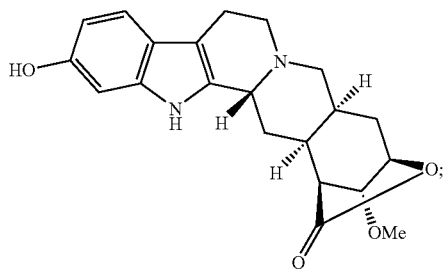
(III)

b) conversion of compound (III) to deserpidic acid lactone (V)

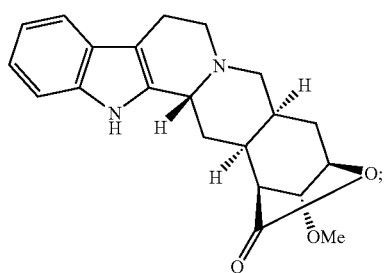
(V)

c) hydrolisis of deserpidic acid lactone (V) to methyl deserpidate (VI)

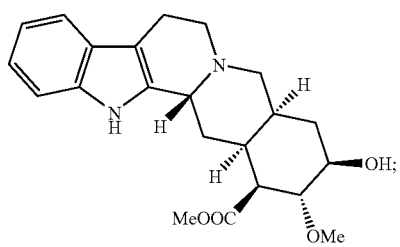
(VI)

d) esterification of methyl deserpidate (VI) with 3,4,5-trimethoxybenzoic acid to give deserpidine (Ia)

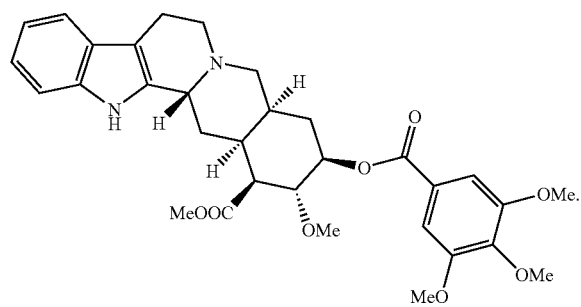
(Ia)

Reserpic acid lactone is a known compound and can be conveniently prepared by hydrolysis of reserpine or rescinnamine, or a mixture thereof, with sodium methoxide to methyl reserpate (Id)

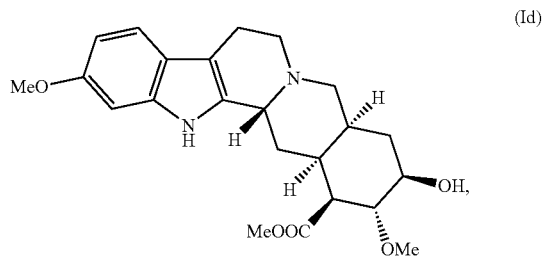
(Id)

which is then cyclized to the corresponding lactone with a procedure similar to the one reported by Woodward (R. B. Woodward et al, Tetrahedron 1958, 2, 1-57). Alternatively, reserpine and rescinnamine can be directly converted to their corresponding lactons according to the literature (H. B. MacPhillamy et al., *J. Am. Chem. Soc.*, 1955, 77, 4335-4343).

The selective demethylation of reserpic acid lactone (step a) can be carried out with conventional demethylating agents, preferably selected from boron tribromide, iodotrimethylsilane and hydriodic acid under reaction conditions that can easily be optimised by the skilled chemist, provided that the lactone's stability is ensured. The use of boron tribromide is particularly preferred, as described in the reported example.

Step b) can be carried out with methods suitable for reducing phenol to benzene. Preferably, this step is carried out transforming compound (III) in a compound of formula (IV)

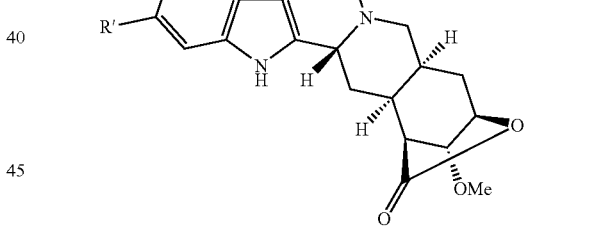
(IV)

in which R' is a leaving group
and reducing (IV).

Among the leaving groups, sulfonic esters, such as tosylate or mesylate, isoureido groups (under the conditions described by Vowinkel in E. Vowinkel et al., Chem. Ber. 1974, 107, 907-914) are preferred, for example those obtained by treatment with dicyclohexylcarbodiimide or diisopropylcarbodiimide, or the (5-phenyl-tetrazolyl)oxy group (obtained by treatment with 1-chloro-5-phenyl-tetrazole under the conditions described by W. J. Musliner et al. *J. Am. Chem. Soc.* 1959, 81, 4271-4273). Particularly preferred is the tosylate group, as described in the reported example.

The reducing agent is, for example, selected from nickel Raney, palladium on charcoal and platinum. Nickel Raney must be used to reduce sulfonic esters, whereas palladium on charcoal is preferred for the reduction of isoureas, for example those obtained with dicyclohexylcarbodiimide or diisopropylcarbodiimide.

The hydrolysis of deserpidic acid lactone to methyl deserpidate (step c) can be carried out with sodium methoxide in alcohols and the esterification of methyl deserpidate to deserpidine (step d) is carried out under conditions analogous to those reported in literature (H. B. MacPhillamy et al., *J. Am. Chem. Soc.*, 1955, 77, 4335-4343; M. Lounasmaa et. al., Heterocycles 1985, 23, 371-375; R. H. Levin et al., *J. Org. Chem.* 1973, 38, 1983-1986).

Therefore, the use of reserpic acid lactone as precursor allows to overcome the regio- and chemoselectivity problems of the known processes. In fact, in the lactone, the conformation of the 16-, 17- and 18-substituents is such that the 17-methoxy group is in the axial position, while in the precursors is in the equatorial position; the axial conformation shields the methoxy group from the attack of demethylating reagents and allows selective demethylation of the 11-position with respect to the 17-position. The process of the invention provides a minimum yield of 40%.

The following examples illustrate the invention in greater detail.

EXAMPLES

Example 1

Synthesis of Methyl Reserpate

A suspension of reserpine (1 g, 0.16 mmol) in a solution of sodium methoxide (0.150 g, 4.8 mmol) in methanol (50 ml) was refluxed until disappearance of the starting material (1 h), then cooled and concentrated under vacuum to one third of the volume. The solution was diluted with water (60 ml) and pH was adjusted to 1 with concentrated hydrochloric acid. The aqueous solution was then repeatedly washed with ethyl ether. The aqueous phase was then alkalinized with concentrated ammonia and repeatedly extracted with methylene chloride (4×30 ml). The combined organic phases were dried over sodium sulfate and concentrated under vacuum to give an amorphous residue (0.66 g), used for the following step without any further purification.

The same process was followed starting from equivalent amounts of rescinnamine.

Example 2

Synthesis of Reserpic Acid Lactone

A) From Reserpine

Reserpine (4.1 g, 6.74 mmol) was added under stirring to a solution of aluminium isopropoxide (10.5 g, 51.4 mmol) in xylene (175 ml) and the resulting mixture was refluxed under nitrogen for 6 hours. The reserpic acid lactone precipitated from the solution was filtered and washed with benzene (3×40 ml), followed by ethyl ether (4×40 ml). The residue was recrystallized from $CHCl_3$ affording 2.07 g (5.45 mmol, 81%) of the desired product. The same procedure was applied to rescinnamine.

B) From Methyl Reserpate

Aluminium isoperoxide (0.747 g, 3.65 mmol) was dissolved under nitrogen in xylene (11.0 ml). Methyl reserpate (0.200 g, 0.483 mmol) was added and the reaction mixture was refluxed with stirring. The ester dissolved quickly and the lactone started to separate as a white solid after 5'. After 2 h under reflux the product was separated by filtration and washed with xylene (3×20 ml), and ether (3×20 ml). The residue was recrystallized from $CHCl_3$ affording 0.168 g (0.440 mmol, 91%) of the desired product.

$^1$H NMR (DMSO-$d_6$, 400 MHz) δ 10.5 (bs, 1H, NH), 7.18 (d, 1 H, J=8.4 Hz, H-9), 6.77 (d, 1 H, J=2.3 Hz, H-12), 6.58 (dd, 1 H, J1=8.4 Hz $J_2$=2.3 Hz, H-10), 4.75 (m, 1 H, J=4.3 Hz), 4.10 (t, 1 H, J=5 Hz, H-17), 3.73 (s, 3H, OMe), 3.45 (d, 1 H, J=12.0 Hz, H-3), 3.35 (s, 3 H, OMe), 2.90 (dd, 1 H, $J_1$=11.0 Hz, $J_2$=5.2 Hz), 2.76-2.63 (m, 1 H), 2.62-2.45 (m, 5 H), 2.43-2.24 (m, 3 H), 2.00 (m, 1 H, $J_1$=15.0 Hz, $J_2$=8.6 Hz), 1.73 (m, 1 H), 1.56 (m, 1 H, $J_1$=15.0 Hz, $J_2$=4.1 Hz, H-19);

$^{13}$C NMR (DMSO-$d_6$, 100 MHz) δ 178.3, 155.7, 137.5, 135.2, 121.9, 118.6, 108.5, 106.7, 95.5, 77.7, 77.1, 58.8, 57.1, 55.9, 54.9, 53.2, 45.5, 35.4, 31.3, 27.7, 26.4, 22.2.

Example 3

Synthesis of 11-O-demethyl Reserpic acid lactone

Reserpic acid lactone (0.210 g, 0.550 mmol) was suspended under argon in anhydrous $CH_2Cl_2$ (8.0 ml) and the mixture was cooled to 0° C. After 15' boron tribromide was added (1.4 ml, 1.37 mmol, 1.0 M solution in $CH_2Cl_2$) and the solution turned brick red. After 5 h the reaction was quenched with a $NaHCO_3$ saturated solution and extracted with $CH_2Cl_2$. The aqueous phases were collected and extracted again with AcOEt (3×15.0 ml). The organic phases were combined and dried. The aqueous phase was filtered, the precipitate was redissolved in a 1:1 THF/MeOH mixture, and added to the previously obtained organic solution. After filtration and concentration under vacuum the solid residue was chromatographed (silica gel, $CH_2Cl_2$/MeOH=15:1, then 16:1) to give the desired product (0.187 g, 0.51 mmol, 92%).

$^1$H NMR (THF-$d_8$, 400 MHz) δ 9.38 (bs, 1 H, NH), 7.54 (bs, 1 H, OH), 7.07 (d, 1 H, J=8.4 Hz, H-9), 6.59 (d, 1 H, J=2.2 Hz, H-12), 6.44 (dd, 1 H, $J_1$=8.4 Hz, $J_2$=2.2 Hz, H-10), 4.63 (t, 1 H, J=4.3 Hz, H-18), 4.03 (t, 1 H), J=5.2 Hz, H-17), 3.61 (d, 1 H, H-3), 3.40 (s, 3 H, OMe), 2.90 (m, 1 H), 2.86-2.46 (m, 7 H), 2.38 (m, 1 H), 2.22 (dd, 1 H, $J_1$=13.5 Hz, $J_2$=2.0 Hz), 2.11 (m, 1 H, $J_1$=14.9 Hz, $J_2$=8.5 Hz), 1.86 (m, 1 H), 1.61 (dd, 1 H, $J_1$=14.8 Hz, $J_2$=3.9 Hz, H-19);

$^{13}$C NMR (THF-$d_8$, 100 MHz) δ 176.6, 153.2, 138.0, 133.9, 121.3, 117.5, 108.4, 106.9, 96.6, 78.2, 76.7, 58.9, 56.2, 54.6, 53.1, 45.7, 35.8, 31.8, 27.9, 26.2, 22.1.

Example 4

Synthesis of 11-O-p-toluenesulfonyl-11-O-demethyl Reserpic Acid Lactone

11-O-Demethyl reserpic acid lactone (0.700 g, 1.90 mmol) was dissolved under nitrogen in 65 ml of anhydrous THF, then triethylamine was added (1.86 ml, 13.32 mmol). The reaction mixture was reacted for 10', added with p-toluenesulfonyl chloride (1.09 g, 5.71 mmol), then refluxed for 42 h. The reaction mixture was evaporated under vacuum and the residue was chromatographed (silica gel, $CH_2Cl_2$/MeOH=17:1), to afford 0.75 g of the desired compound (0.75 g, 1.44 mmol 76%).

$^1$H NMR (THF-$d_8$, 400 MHz) δ 9.99 (bs, 1 H, NH), 7.63 (2 H, Ar), 7.31 (2 H, Ar), 7.15 (d, 1 H, J=8.4 Hz, H-9), 6.90 (d, 1 H, J=2.2 Hz, H-12), 6.47 (dd, 1 H, $J_1$=8.4 Hz, $J_2$=2.2 Hz, H-10), 4.64 (t, 1 H, J=4.1 Hz, H18), 4.03 (t, 1 H, J=5.2Hz, H-17), 3.62 (d, 1 H, J=11.8 Hz, H-3), 3.39 (s, 3 H, OMe), 2.91 (m, 1 H), 2.84-2.43 (m, 7 H), 2.38 (m, 4 H, 1 Me and 1 H), 2.22 (dd, 1 H, $J_1$=13.5 Hz, $J_2$=2.0 Hz), 2.10 (m, 1 H, $J_1$=15.0 Hz, $J_2$=8.5 Hz), 1.86 (m, 1 H), 1.60 (dd, 1 H, $J_1$=15.0 Hz, $J_2$=4.0 Hz, H-19);

$^{13}$C-NMR (THF-d$_8$, 100 MHz) δ 176.7, 144.9, 144.8, 136.2, 133.5, 129.6, 128.7, 126.3, 117.4, 113.2, 107.5, 105.0, 78.2, 76.7, 58.8, 56.3, 54.5, 52.9, 45.7, 35.7, 31.7, 29.9, 27.9, 26.2, 21.9, 20.8.

Example 5

Synthesis of Deserpidic Acid Lactone

Ni-Raney, previously washed with H$_2$O (twice), MeOH (twice) and EtOH (once) was introduced (4.86 g, humid) into a hydrogenation reactor under argon, followed by 11-O-p-toluenesulfonyl-11-O-demethylreserpic acid lactone (0.300 g, 0.58 mmol), dissolved in 14 ml of anhydrous THF and 16.0 ml of EtOH. The hydrogenation was carried out under a pressure of 50 psi. After 8 h the solution was filtered through Celite, washed with CHCl$_3$ (6×40 ml) and 100 ml of MeOH. The solvent was evaporated under vacuum and the residue was chromatographed (silica gel, CH$_2$Cl$_2$/MeOH=20:1), to afford 0.17 g of the desired compound (0.170 g, 0.49 mmol, 85%).

$^1$H NMR (THF-d$_8$, 400 MHz) δ 9.80 (bs, 1H, NH), 7.32 (d, 1 H, J=7.8 Hz, H-9), 7.20 (d, 1 H, J=7.6 Hz, H-12), 6.98-6.87 (m, 2 H, Ar, H-10, H-11), 4.04 (t, 1 H, J=5.2 Hz, H-17), 3.66 (d, 1 H, J=11.8 Hz, H-3), 3.40 (s, 3H, OMe), 2.94 (m, 1 H), 2.84 (m, 1H), 2.78-2.33 (m, 7H), 2.28 (dd, 1 H, J$_1$=13.7 Hz, J$_2$=2.0 Hz), 2.12 (m, 1 H, J$_1$=15.0 Hz, J$_2$=8.5 Hz), 1.89 (m, 1 H), 1.62 (dd, 1 H, J$_1$=14.8 Hz, J$_2$=4.0 Hz, H-19);

$^{13}$C-NMR (THF-d$_8$, 100 MHz) δ 176.7, 136.9, 136.1, 127.6, 120.2, 118.3, 117.4, 110.5, 107.2, 78.2, 76.7, 58.9, 56.2, 54.6, 53.1, 45.7, 35.8, 31.7, 27.9, 26.2, 22.1.

Example 6

Synthesis of Methyl Deserpidate

Deserpidic acid lactone (0.140 g, 0.398 mmol) was dissolved under nitrogen in 27.0 ml of anhydrous MeOH. This suspension was added with MeONa (0.032 g, 0.597 mmol), then the mixture was reacted under reflux for 90'. The reaction was quenched adding 0.2 ml of glacial acetic acid and the solvent was evaporated under vacuum. The resulting product was redissolved with a 0.2 M NaOH solution and extracted with CHCl$_3$ (4×25 ml); the organic phase was dried and filtered. The solvent was evaporated under vacuum and the residue was chromatographed (silica gel, CH$_2$Cl$_2$/MeOH 10:1), to afford 0.17 g of the desired product (0.170 g, 0.38 mmol, 95%).

$^1$H NMR (CDCl$_3$, 400 MHz) δ 7.80 (bs, 1 H, NH), 7.46 (d, 1 H, J=6.8 Hz), 7.31 (d, 1 H, J=8.0 Hz), 7.14 (dt, 1 H, J=6.8 Hz, J$_2$=1.2 Hz), 7.09 (dt, 1 H, J$_1$=7.6 Hz, J$_2$=1.2 Hz) 4.46 (bs, 1 H, H-3), 3.79 (s, 3 H, OMe), 3.62-3.48 (m, 5 H, 1 OMe and 2 H), 3.26-3.15 (m, 2 H), 3.06-2.91 (m, 2 H), 2.59-2.45 (m, 3 H), 2.32-2.17 (m, 2 H), 2.03-1.91 (m, 1 H), 1.89-1.71 (m, 3 H);

$^{13}$C-NMR (CDCl$_3$, 100 MHz) δ 173.7, 135.7, 132.1, 127.8, 121.7, 119.7, 118.3, 111.1, 108.3, 81.6, 75.3, 61.2, 53.9, 52.1, 51.5, 51.3, 49.5, 34.7, 33.0, 32.4, 24.5, 16.9.

Example 7

Synthesis of Deserpidine

Methyl deserpidate (0.5 g, 1.30 mmol) was dissolved under nitrogen in dry pyridine (4.0 ml). 3,4,5-Trimethoxybenzoyl chloride (0.5 g, 2.17 mmol) was dissolved in benzene (2 ml), then dropped slowly in the reaction mixture. The reaction was kept under stirring for 5 days at 5° C. and then quenched with 50 ml of water. This solution was added with a mixture of concentrated NH$_3$ (2 ml) in 10 ml of H$_2$O. The solution was then extracted with CH$_2$Cl$_2$ (3×25 ml) and the organic phase was dried and filtered. The solvent was evaporated under vacuum and the resulting residue was recrystallized from acetone, to afford 0.168 g (0.440 mmol, 91%) of the desired product.

$^1$H-NMR (CDCl$_3$, 400 MHz) δ 7.83 (bs, 1 H, NH), 7.48 (1 H), 7.33 (s, 1 H), 7.33 (s, 1 H), 7.32 (1 H), 7.17 (1 H), 7.12 (1 H), 5.07 (1 H), 4.52 (bs, 1 H, H-3), 3.90 (dd, 1 H, J$_1$=12 Hz, J$_2$=9 Hz), 3.89 (s, 3 H, OMe), 3.89 (s, 3 H, OMe), 3.89 (s, 3 H, OMe), 3.80 (s, 3 H, OMe), 3.80 (s, 3 H, OMe), 3.20 (m, 1 H), 3.20 (m, 1 H), 3.04 (dd, 1 H, J$_1$=12 Hz, J$_2$=4 Hz), 2.98 (1 H), 2.70 (dd, 1 H, J$_1$=12 Hz, J$_2$=5 Hz), 2.54 (1 H), 2.47 (dd, 1 H, J$_1$=12 Hz, J$_2$=2 Hz), 2.34 (m, 1 H), 2.33 (1 H), 2.04 (1 H), 1.98 (1 H), 1.90 (1 H), 1.86 (1 H);

$^{13}$C-NMR (CDCl$_3$, 100 MHz) δ 176.8, 169.4, 163.8, 161.0, 159.4, 144.0, 141.6, 141.6, 141.4, 140.1. 137.4, 133.1, 133.0, 115.5, 115.5, 86.2, 85.5, 82.3, 75.4, 74.0, 72.1, 67.8, 65.3, 61.8, 57.2, 50.7, 39.8, 27.3, 20.3.

The invention claimed is:

1. A process for the preparation of deserpidine (Ia)

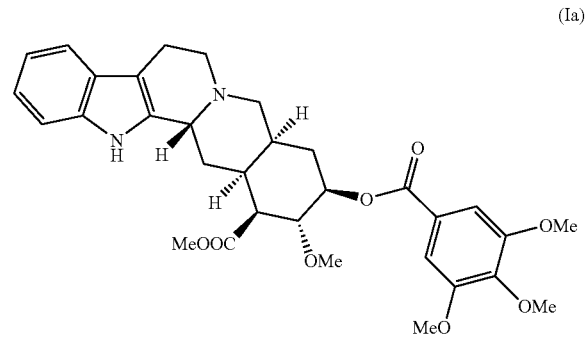

comprising the following steps:
 a) demethylation of reserpic acid lactone (II)

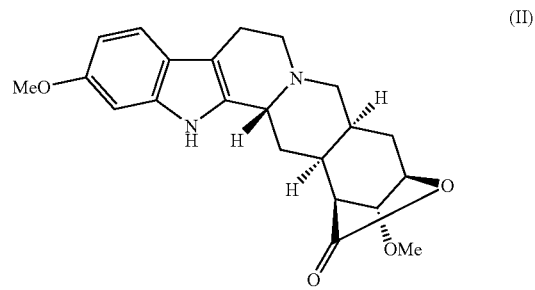

to give 11-O-demethyl reserpic acid lactone (III)

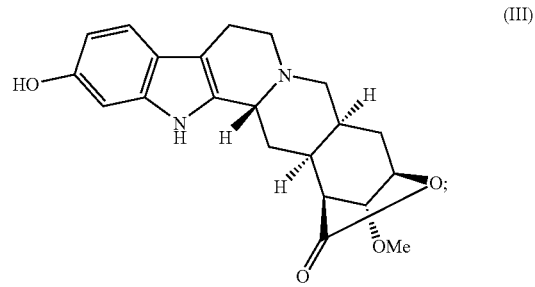

b) conversion of compound (III) to deserpidic acid lactone (V)

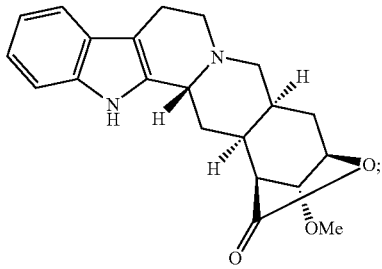

c) hydrolisis of deserpidic acid lactone (V) to methyl deserpidate (VI)

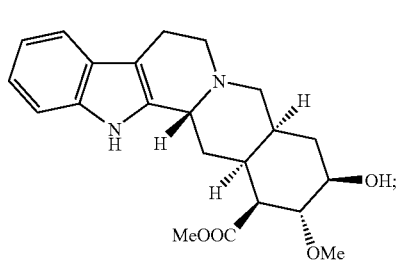

d) esterification of methyl deserpidate (VI) with trimethoxybenzoic acid to give deserpidine (Ia).

2. The process as claimed in claim 1 wherein the conversion of compound (III) to deserpidic acid lactone (V) is carried out trasforming compound (III) into a compound of formula (IV)

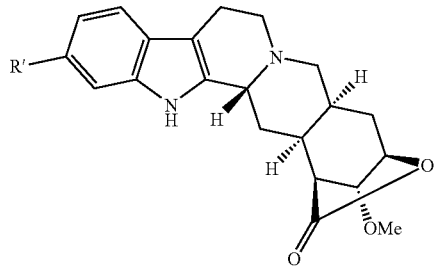

in which R' is a leaving group
and reducing compound (IV).

3. The process as claimed in claim 2 in which in compound (IV) the R' group is selected from a sulfonate, an isoureido or a (5-phenyl-tetrazolyl)oxy group.

4. The process as claimed in claim 3 in which the R' group is p-toluenesulfonate or methanesulfonate.

5. The process as claimed in claim 4 in which the R' group is p-toluenesulfonate.

6. The process as claimed in claim 5 in which the reduction of compound (IV) is carried out with nickel Raney.

7. The process as claimed in claim 3 in which the R' group is an isoureido group.

8. The process as claimed in claim 7 in which the reduction of compound (IV) is carried out with palladium on charcoal.

9. The compound of formula (III)

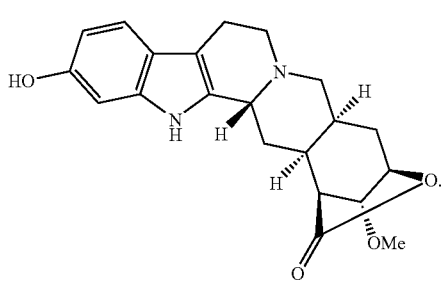

* * * * *